United States Patent [19]

Forestier et al.

[11] Patent Number: 5,145,662

[45] Date of Patent: Sep. 8, 1992

[54] COSMETIC USE OF DIBENZOYLMETHANE DIORGANOPOLYSILOXANES AND NOVEL COSMETIC COMPOSITIONS CONTAINING SUCH COMPOUNDS FOR THE PROTECTION OF SKIN AND HAIR

[75] Inventors: Serge Forestier, Claye-Souilly; Gerard Lang, Saint-Gratien; Herve Richard, Paris, all of

[73] Assignee: L'Oreal, Paris, France

[21] Appl. No.: 479,524

[22] Filed: Feb. 13, 1990

[30] Foreign Application Priority Data

Feb. 15, 1989 [FR] France .................. 89 01991

[51] Int. Cl.$^5$ .............. A61K 9/12; A61K 7/025; A61K 7/06; A61K 7/04
[52] U.S. Cl. ..................... 424/45; 424/47; 424/59; 424/60; 424/61; 424/63; 424/64
[58] Field of Search ............ 424/59, 60, 47, 61, 424/63, 64, 70, 71, 78, DIG. 1, DIG. 2, DIG. 5; 252/DIG. 13; 514/772, 844, 845, 937, 935, 944, 945

[56] References Cited

U.S. PATENT DOCUMENTS

| | | | |
|---|---|---|---|
| 4,489,057 | 12/1984 | Welters et al. | 424/60 X |
| 4,696,969 | 9/1987 | Thimineur et al. | 524/762 |
| 4,814,162 | 3/1989 | Lang et al. | 424/63 X |

FOREIGN PATENT DOCUMENTS 0138590 4/1985 European Pat. Off. .
WO8809663 12/1988 PCT Int'l Appl. .
2185396 7/1987 United Kingdom .

*Primary Examiner*—Thurman K. Page
*Attorney, Agent, or Firm*—Marshall, O'Toole, Gerstein, Murray & Bicknell

[57] ABSTRACT

The cosmetic use is described, for use as a UV filter, of dibenzoylmethane diorganopolysiloxanes having either formula:

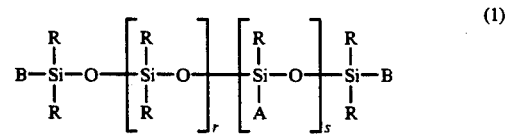

where R is $C_1$-$C_{10}$ alkyl, phenyl or 3,3,3-trifluoropropyl, B is R or A, r=0–200, s=0–50, or formula:

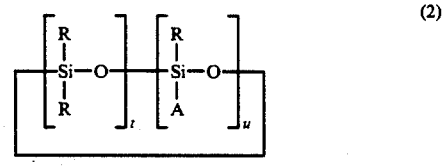

where u=1–20, t=0–20 and t+u≧3. A and/or B represent an alkylene or alkyleneoxy-dibenzoylmethane which may be substituted.

13 Claims, No Drawings

COSMETIC USE OF DIBENZOYLMETHANE DIORGANOPOLYSILOXANES AND NOVEL COSMETIC COMPOSITIONS CONTAINING SUCH COMPOUNDS FOR THE PROTECTION OF SKIN AND HAIR

The present invention concerns the cosmetic use of dibenzoylmethane diorganopolysiloxanes, particularly as UV filters, as well as novel cosmetic compositions containing such compounds for the protection of skin and hair.

Light of wavelengths between 280 nm and 400 nm is known to cause browning of the human epidermis; radiation of wavelengths between 280 nm and 320 nm known as UV-B causes erythema and cutaneous burns which may hinder the development of a tan; UV-B radiation must therefore be filtered out.

It is further known that UV-A radiation, with wavelengths between 320 nm and 400 nm, promotes browning of the skin and is likely to damage it, particularly with sensitive skin or where the skin is continually exposed to the sun's rays. In particular, UV-A radiation causes loss of skin elasticity and the appearance of lines resulting in premature ageing. It promotes the erythmatic reaction or amplifies it in some cases and may even be the cause of phototoxic or photallergenic reactions.

It is desirable therefore to design UV absorbing compounds so that they absorb a wide band of UV radiation in order to filter out both UV-A and UV-B.

It is further known that constituents of cosmetic preparations do not always have sufficient light stability and degrade when exposed to light.

It is thus desirable to incorporate UV filtering compounds into such preparations. These filters must also be stable and have sufficient solubility in media normally used in cosmetics, in particular oils and fats.

With hair, it is also desirable to protect it against photochemical degradation, particularly discolouring or change of shade.

Grafting molecules having a UV filtering effect onto polymer chains such as synthetic carbon polymers, natural polymers, protein hydrolysates or polyaminoamides is also known. Graft polymers as described, for example, in French patents numbers 2 197 023, 2 237 912, 2 531 960, 2 548 018, 2 549 069, 2 586 692 and 2 586 693 may be used to prepare cosmetic compositions for protection of human skin or as sun screens. However, graft polymers generally have low solubility in the usual cosmetic solvents, particularly in oily supports, and they form films having too rigid a structure.

The applicant has now discovered that, surprisingly, certain dibenzoylmethane diorganopolysiloxanes have good cosmetic properties and good filtering properties over a wide range of wavelengths, from 280 nm to 360 nm. In particular they have excellent liposolubility and can thus be used in the fatty supports used in cosmetics. Apart from their good filtering powers and good solubility in oily media and the usual cosmetic solvents, these dibenzoylmethane diorganopolysiloxanes also have excellent chemical and photochemical stability and soften the skin and hair, which tolerate them well.

An object of the present invention is, then, the cosmetic use of dibenzoylmethane diorganopolysiloxanes, particularly as UV filtering agents for radiation of wavelengths between 280 nm and 360 nm, selected from those having the formula:

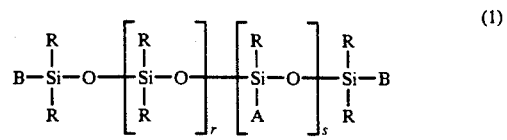

wherein:

R may be the same for each occurrence or different and is selected from linear or branched $C_1$-$C_{10}$ alkyl radicals, phenyl radicals and 3,3,3-trifluoropropyl radicals, at least 80% by number of the R radicals being methyl radicals, B may be the same for each occurrence or different and is selected from radicals R and A, r is a number between 0 and 200 inclusive, s is a number between 0 and 50 inclusive and if s is 0 at least one of the two B radicals is A; and from those having the formula:

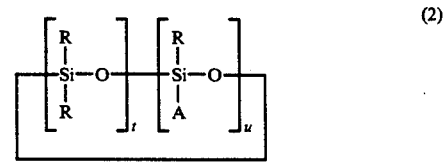

wherein:

R has the meaning defined for formula (1), u is a number between 1 and 20 inclusive, t is a number between 0 and 20 inclusive, t+u is greater than or equal to 3; and wherein in both formulae the symbol A denotes a radical having the formula:

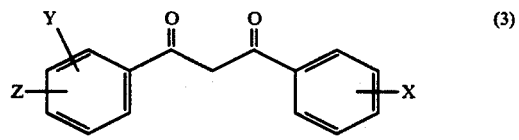

wherein:

X is selected from a hydrogen atom, a linear or alkoxy radical,

Y is selected from a hydrogen atom, a hydroxy group and a linear or branched $C_1$-$C_4$ alkoxy radical, Z is a divalent moiety with the formula:

wherein is 0 or 1, p is a whole number between 1 and 10 inclusive and W is selected from a hydrogen atom and a $C_1$-$C_4$ alkyl radical providing that, when m equals 0, Y represents an alkoxy or OH radical and is ortho to Z.

The following linear or branched alkyl radicals merit particular mention: methyl, ethyl, n-propyl, isopropyl, n-butyl, isobutyl, tertbutyl, n-amyl, isoamyl, neopentyl, n-hexyl, n-heptyl, n-octyl, 2-ethylhexyl and tert-octyl.

The following linear or branched alkoxy radicals merit particular mention: methoxy, ethoxy, n-propoxy, isopropoxy, n-butoxy, isobutoxy, tert-butoxy, n-amyloxy, isoamyloxy, neopentyloxy, n-hexyloxy, n-heptyloxy, n-octyloxy, 2-Ethylhexyloxy and tert-octyloxy.

Particularly preferred polymers are random or block polymers having formula (1) or (2) with at least one of the following features:

R is methyl,
B is methyl,
r is between 5 and 20 inclusive,
s is between 2 and 15 inclusive,
t+u is between 3 and 10 inclusive,
X is H,
Y is H, hydroxy or methoxy,
Z is divalent moiety wherein m=0 or 1, p=1, W=H or methyl.

Preparation of polymers with formula (1) and (2) may start from the corresponding polymer wherein all the A radicals are hydrogen.

This polymer is denoted by SiH; SiH groups may be present within the chain and/or at its extremities. These SiH polymers are well known in the silicone industry and are generally commercially available.

They are described, for example, in American patents U.S. Pat. Nos. 3,220,972, 3,436,366, 3,697,473 and 4,340,709.

SiH polymers may thus be selected from those having the formula:

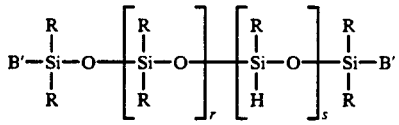
(4)

where R, r and s have the meanings given above for formula (1) and radicals B', which may be the same for each occurrence or different, are selected from radicals R, a hydrogen atom and those having the formula:

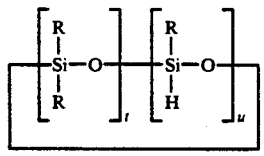
(5)

where R, t and u have the meanings given above for formula (2).

SiH polymers having formula (4) or (5) are reacted by hydrosilylation in the presence of a catalytic quantity of a platinum catlyst or an organic dibenzoylmethane derivative selected from those having the formula:

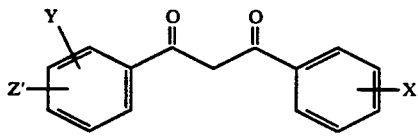
(6)

where X, and Y have the meaning given above for formula (3) and Z' represents an unsaturated monovalent radical with formula:

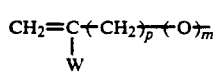

wherein p, m and W have the meaning given for formula (3) above providing that when m equals 0, Y represents a hydroxy or alkoxy radical and is ortho to Z'.

Products with formula (6) are, for the most part, known. They may in particular be synthesised by the methods described in the publications referred to in the following CHEMICAL ABSTRACTS: Vol. 58, 11316e, Vol. 93, 8051h, Vol. 101, 191435g and Vol. 94, 308660p, and in patent documents FR-A-2 506 156, FR-A-2 513 992 and FR-A-2 526 658.

The following method is suitable for m=0:

In a first stage, 2,3,4-position hydroxylated acetophenone is reacted with an alkenyl halide with formula:

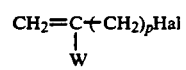
(7)

where W and p have the meaning given above for formula (6) and Hal represents a halogen atom, preferably chlorine or bromine. This is conducted in the presence of a base, for example an alkali or alkaline earth metal hydroxide or carbonate or an alkaline amide, alcoholate or hydride, in a solvent which is compatible with that base, such as water or an organic solvent such as dioxane, dimethylsulphoxide or dimethylformamide, at a temperature between room temperature and the boiling point of the solvent. This produces a product with the formula:

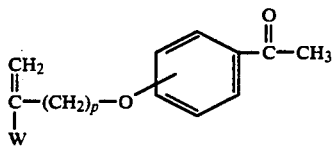
(8)

During a second stage b) a CLAISEN rearrangement, as described by TARBELL (Organic Reactions, Vol. 2, John WILEY, New York, 1944, page 1), is carried out by heating the compound with formula (8) to at least about 170° C., if necessary in the presence of a solvent, to obtain a product with the formula:

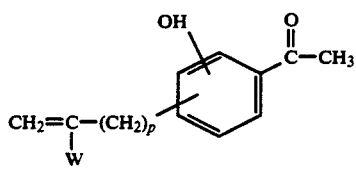
(9)

During a third stage c) the product with formula (9) is condensed with a benzoyl chloride with the formula:

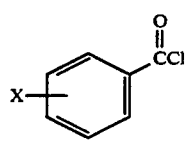
(10)

in pyridine to produce a product with the formula:

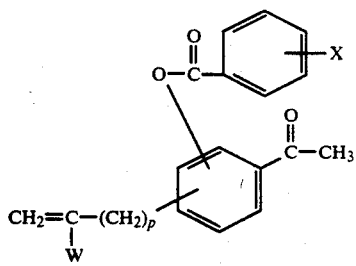

(11)

and the product with formula (6) with m=0 is obtained following a fourth stage d), a BAKER VENKATARAMAN rearrangement of the product with formula (11) in pyridine in the presence of potassium.

Compounds with formula (6) where m=0 or 1 and Y is other than hydroxy are obtained by condensation of an ester with formula (12) with an acetophenone with formula (13):

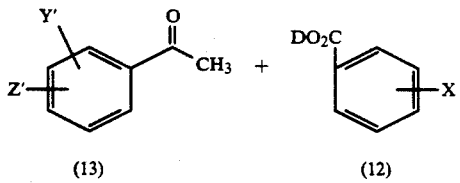

In the compound with formula (12), X has the meaning given above for formula (3) and D represents a $C_1$–$C_6$ alkyl moiety. In the compound with formula (13), Z' has the meaning given above for formula (6) and Y' represents a hydrogen atom or a $C_1$–$C_4$ alkoxy radical. The reaction is carried out in the presence of a base, for example an alkaline alcoholate, hydride or amide in a solvent which is compatible with the base such as toluene, isopropyl ether, dioxane, tetrahydrofurane, 1,2-dimethoxyethane, dimethylsulphoxide or dimethyl-formamide, at a temperature between room temperature and the boiling point of the solvent.

Acetophenone with formula (13) may be prepared using known methods, for example:

when m=1 and Y'=H, the acetophenone can be obtained using the method described above for the preparation of the compound with formula (8), when m=0 and Y'=$C_1$–$C_4$ alkoxy, the acetophenone is obtained by alkylation of the compound with formula (9) using a halide or $C_1$–$C_4$ alkyl sulphate using the method described in stage a) above.

Platinum catalysts used for hydrosilylation of the polymers with formula (4) or (5) with the organic derivative with formula (6) are amply described in the literature. Complexes of platinum and an organic product merit particular mention. These are described in American patents U.S. Pat. Nos. 3,159,601, 3,159,602 and 3,220,972 and in European patents EP-A-57 459, EP-A-188 978 and EP-A-190 530. American patents U.S. Pat. Nos. 3,419,593, 3,377,432 and 3,814,730 describe other complexes of platinum and a vinylated organopolysiloxane.

For the reaction of the SiH polymer having formula (4) or (5) on the derivative with formula (6), the amount of platinum catalyst used comprises between 5 and 660 ppm, calculated by weight of platinum metal, preferably between 10 and 200 ppm based on the weight of SiH polymer with formula (4) or (5).

The hydrosilylation reaction may take place in the dry state or using a volatile organic solvent such as toluene, heptane, xylene, tetrahydrofurane or tetrachloroethylene.

It is generally desirable to heat the reaction mixture to a temperature of 60° to 120° C. for the time necessary to complete the reaction. The SiH polymer may be added dropwise to a solution of the derivative with formula (6) in an organic solvent containing the catalyst. The SiH polymer and the derivative with formula (6) may also be added simultaneously to a suspension of the catalyst in an organic solvent.

Reaction completeness is verified by titrating residual SiH against alcoholic potash. The solvent is then eliminated, for example by distillation under reduced pressure.

The crude oil obtained can be purified, for example by passage over an absorbent silica column.

A further object of the invention is constituted by cosmetic compositions to protect the skin and hair against UV radiation, containing an effective quantity of a dibenzoylmethane diorganopolysiloxane with formula (1) or (2), in a cosmetically acceptable medium.

A further object of the invention is a method of protecting skin and natural or sensitised hair against solar radiation, consisting in applying to the skin or hair an effective quantity of at least one compound having formula (1) or (2) in an acceptable cosmetic support comprising at least one oily phase.

"Sensitised hair" means hair which has been permed, dyed or bleached.

A still further object of the invention is a tinted or untinted, light stable cosmetic composition comprising an effective quantity of at least one dibenzoylmethane diorganopolysiloxane having formula (1) or (2).

When used as a composition for protecting the human epidermis against ultraviolet radiation, the preparation may be in many of the diverse forms commonly used for this type of cosmetic composition. In particular, oily, alcoholic or oleoalcoholic lotions may be used, also emulsions such as creams or milks, oleoalcoholic, alcoholic or hydroalcoholic gels, solid sticks or aerosols.

It may contain any cosmetic additives normally used in this type of composition, such as thickeners, softeners, moisturisers, surfactants, preservatives, anti-foaming agents, perfumes, oils, waxes, lanolin, propellants, dyes and/or pigments to colour the composition itself or the skin, or any other ingredient normally used in cosmetics.

Compound (1) or (2) is present in proportions of between 0.25 and 3% by weight with respect to the total weight of the protective cosmetic composition for the human epidermis.

As solubilising solvent, an oil may be used, or a wax or generally any oily body, a monoalcohol or a low polyol, or a $C_{12}$–$C_{15}$ alcohol benzoate or a mixture thereof. Particularly preferred monoalcohols or polyols are ethanol, isopropanol, propyleneglycol, glycerine or sorbitol.

One embodiment of the invention is an emulsion in the form of a protective cream or milk comprising, as well as the compound with formula (1) or (2), fatty alcohols, fatty acid esters in particular fatty acid triglycerides, fatty acids, lanolin, natural or synthetic oils or waxes and emulsifiers, in the presence of water.

A further embodiment is constituted by oily lotions with bases of natural or synthetic oils or waxes, lanolin and fatty acid esters, in particular fatty acid triglycerides, or by oleoalcoholic lotions with a low alcohol base such as ethanol or a glycol such as propyleneglycol and/or a polyol such as glycerine and oils, waxes and fatty acid esters such as fatty acid triglycerides.

The cosmetic composition of the invention may also be in the form of an alcoholic gel comprising one or more alcohols or low polyols such as ethano propyleneglycol or glycerine and a thickener such as silica. Oleoalcoholic gels further contain a natural or synthetic oil or wax.

Solid sticks are constituted by natural or synthetic waxes and oils, fatty alcohols, fatty acid esters, lanolin and other oily substances.

For aerosol type compositions, standard propellants such as alkanes, fluoroalkanes and chlorofluoroalkanes are used.

The scope of the present invention also covers sun screening cosmetic compositions containing at least one compound with formula (1) or (2) and which may contain other UV-B and/or UV-A filters.

In this case the total quantity of filters present in the sun screen composition, i.e. the compound with formula (1) or (2) and other filters if any, lies between 0.5 and 15% by weight with respect to total sun screen composition weight.

The forms described above for the human skin protection compositions may also be used for these sun screen compositions.

When the inventive cosmetic composition is intended to protect natural or sensitised hair from UV radiation the composition may be in the form of a shampoo, lotion, gel or rinsing emulsion, for application before or after shampooing, before or after dyeing or bleaching, before or after a perm, as a styling or treating gel, brushing or setting gel or lotion, hairspray or lacquer. As well as the inventive compound the composition may contain any of the additives used in this type of composition such as surfactants, thickeners, polymers, softeners, preservatives, foam stabilisers, electrolytes, organic solvents, siliconised derivatives, oils, waxes, degreasing agents, dyes and/or pigments to colour the composition itself or the hair or any other ingredient which is normally used in hairdressing.

It contains 0.25% to 5% by weight of the compound with formula (1) or (2).

The present invention further provides a cosmetic composition containing at least one compound with formula (1) or (2) as a protective agent against ultraviolet radiation constituted as a hairdressing composition such as a hair lacquer, a setting lotion possibly for treating or untangling, a tinting shampoo, a hair dye composition, a cosmetic composition such as nail polish, a treatment cream or oil for the skin, a foundation, a lipstick, a skin care composition such as a bath oil or cream and any other cosmetic composition which, because of its ingredients may lack light stability during storage.

Such compositions contain 0.25 to 3% by weight of the compound with formula (1) or (2).

The invention further envisages a method for protecting cosmetic compositions against ultraviolet radiation consisting in incorporating an effective quantity of at least one compound with formula (1) or (2) into these compositions.

The following examples illustrate the invention without limiting its scope.

EXAMPLE 1

Preparation of a random polymer of formula:

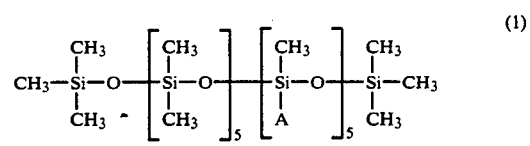

wherein A represents the moiety of formula:

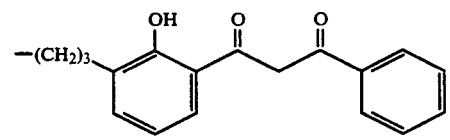

A solution in toluene of 12.6 g (45 meq) 3-allyl-2-hydroxy-5-dibenzoylmethane and 5.12 g polymethylhydrogenodimethylsiloxane having the above formula where A is an atom of hydrogen was added dropwise over one hour 30 minutes to a suspension of 5% (70 mg) platinum on carbon in dry toluene (5 ml) at 90°-100° C. under nitrogen and agitation.

The temperature was maintained throughout at 100° to 105° C., the mixture was stirred and refluxed until the SiH groups had disappeared (absence of 2 180 cm$^{-1}$ infrared band), i.e. for ten hours. It was filtered over paper, the solvent eliminated and washed three times with 80% ethanol. The oil obtained was taken up in chloroform, dried over sodium sulphate and filtered over celite to eliminate the remaining colloidal platinum. After evaporation of the solvent a thick orange-yellow oil was obtained (weight: 9.3 g, yield: 68%).

| UV spectrum (CHCl$_3$): | $\lambda$ max$_1$: | 346 nm |
|---|---|---|
| | $\lambda$ max$_2$: | 365 nm |

Nuclear magnetic resonance analysis ($^1$H and $^{29}$Si) indicated that the product had the desired structure.

EXAMPLE 2

Preparation of a random polymer with the same formula as in Example 1 except that A is a moiety with formula:

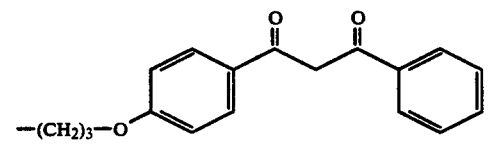

The same method was used as for Example 1 with 10 g (36 meq) 4-allyloxydibenzoylmethane and 5.8 g polymethylhydrogenodimethylsiloxane. A thick yellow oil was obtained (weight: 15 g, yield: 95%).

UV spectrum (CHCl$_3$):$\lambda$max$_1$:353 nm

Nuclear magnetic resonance analysis ($^1$H and $^{29}$Si) indicated that the product had the formula of the polymer given above.

| EXAMPLES OF USE |
|---|
| Example A: oil-in-water sun screen emulsion |

| EXAMPLES OF USE | |
|---|---|
| Compound from example 2 | 2.0 g |
| 2-hydroxy-4-methoxybenzophenone | 1.0 g |
| Liquid lanolin | 7.0 g |
| Triglycerides of myristic/palmitic/stearic acids ("NESATOL" from VEVY) | 5.0 g |
| Oxyethylenated oleic triglycerides ("LUBRAFIL M1969 CS" from GATTEFOSSE) | 2.5 g |
| Mixture of glycerol monostearate and polyethylene glycol stearate (100 OE) ("ARLACEL 165" from SEPPIC) | 5.0 g |
| Stearyl alcohol | 1.0 g |
| Stearic acid | 2.5 g |
| Mixture of cetyl phosphates and diethanolamine monocetyl phosphate ("AMPHISOL NP" from GIVAUDAN) | 0.5 g |
| $C_{12}/C_{15}$ alcohol benzoates ("FINSOLV TN" from WITCO) | 9.0 g |
| Triethanolamine | 0.2 g |
| Preservative | 0.4 g |
| Perfume | 0.6 g |
| Demineralised water qsp | 100 g |
| Example B: (protective cream for the human epidermis) oil-in-water emulsion | |
| Compound from example 1 | 3.0 g |
| Mixture of cetylstearate alcohol and oxyethylenated cetylstearyl alcohol, 33 moles of OE ("SINNOWAX AO" from HENKEL) | 7.0 g |
| Glycerol monostearate | 2.0 g |
| Cetyl alcohol | 1.3 g |
| Propylene glycol | 10.0 g |
| Preservative | 0.2 g |
| Perfume | 0.6 g |
| $C_{12}/C_{15}$ alcohol benzoates ("FINSOLV TN" from WITCO) | 15.0 g |
| Demineralised water qsp | 100 g |

These emulsions were prepared by heating the oily substances and emulsifiers to 80°-85° C. then adding the dibenzoylmethane diorganopolysiloxane. Alternatively the water containing the hydrosoluble compounds is heated to 80°-85° C. and the oily phase added to the aqueous phase. After ten minutes of brisk agitation the emulsion is allowed to cool under moderate agitation and the perfume and preservative added at about 40° C.

We claim:

1. A cosmetic composition which comprises in a cosmetically acceptable medium an effective quantity for filtering UV radiation of wavelengths between 280 nm and 360 nm of at least one dibenzoylmethane diorganopolysiloxane having the formula:

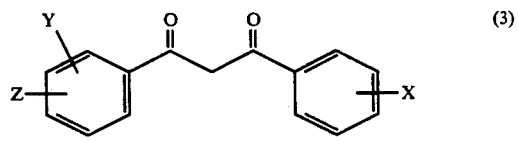

wherein
R may be the same for each occurrence or different and is selected from linear or branched $C_1$-$C_{10}$ alkyl radicals, phenyl radicals and 3,3,3-trifluoropropyl radicals, at least 80% by number of the R radicals being methyl radicals,
B may be the same for each occurrence or different and is selected from radicals R and A,
r is a number between 0 and 200 inclusive,
s is a number between 0 and 50 inclusive and if s is 0 at least one of the two B radicals is A;
and from those having the formula:

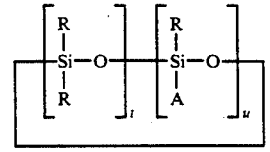

wherein:
R has the meaning defined for formula (1),
u is a number between 1 and 20 inclusive,
t is a number between 0 and 20 inclusive,
t+u is greater than or equal to 3; and wherein in both formulae the symbol A denotes a radical having the formula:

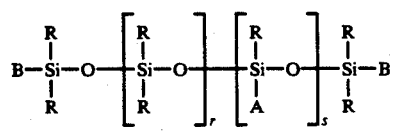

wherein:
X is selected from a hydrogen atom, a linear or branched $C_1$-$C_8$ alkyl radical and a linear or branched $C_1$-$C_8$ alkoxy radical,
Y is selected from a hydrogen atom, a hydroxyl group and a linear or branched $C_1$-$C_4$ alkoxy radical,
Z is a divalent moiety with the formula:

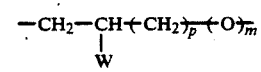

wherein m is 0 or 1, p is a whole number between 1 and 10 inclusive and W is selected from a hydrogen atom and a $C_1$-$C_4$ alkyl radical, provided that when m equals 0, Y represents an alkoxy radical or hydroxy and is ortho to Z.

2. A cosmetic composition according to claim 1 which comprises a random or block dibenzoylmethane diorganopolysiloxane having at least one of the following features: R is methyl, B is methyl, r is between 5 and 20 inclusive, s is between 2 and 15 inclusive, t+u is between 3 and 10 inclusive, X is H, Y is OH or methoxy when m is 0, Y is H, OH, or methoxy when m is 1, p is 1, and W is H or methyl.

3. A cosmetic composition according to claim 1 which comprises a polydimethylsiloxane grafted with 2-hydroxy-3-allyldibenzoylmethane having formula (1) according to claim 1 wherein R and B represent a methyl group, r=5, s=5.

4. A cosmetic composition according to claim 1 which comprises a polydimethylsiloxane grafted with 4-allyloxydibenzoylemthane with formula (1) wherein R and B represent methyl, r=5, s=5.

5. A cosmetic composition according to claim 1 which additionally contains cosmetic additives selected from thickeners, softerners, moisturisers, surfactants, preservatives, anti-foaming agents, perfumes, oils, waxes, lanolin, low monoalcohols and polyols, $C_{12}$-$C_{15}$ alcohol benzoates, propellants, dyes and pigments.

6. A cosmetic composition according to claim 1 which is in the form of an oily, alcoholic or oleoalcoholic lotion, emulsion, oleoalcoholic, alcoholic or hydroalcoholic gel, solid stick, spray or aerosol.

7. A cosmetic composition according to claim 1 which constitutes a protective composition for the human skin and contains 0.25 to 3% by weight of diorganopolysiloxane having formula (1) or (2).

8. A cosmetic composition according to claim 1 in the form of a sun screen which contains 0.5 to 15% by weight of diorganopolysiloxane having formula (1) or (2).

9. A sun screening cosmetic composition according to claim 8 which further contains a filtering agent for UV-B or UV-A radiation.

10. A cosmetic composition according to claim 1 for application to the hair which is in the form of a shampoo, lotion, rinsing gel or emulsion, for application before or after shampooing, before or after dyeing or bleaching, before or after a perm, as a styling or treatment lotion or gel, a brushing or setting lotion or gel, hair spray or hair lacquer and comprises 0.25 to 5% by weight of diorganopolysiloxane having formula (1) or (2).

11. A cosmetic composition according to claim 1 in the form of a coloured or non-coloured cosmetic composition which is constituted by a hairdressing composition, a cosmetic or a product for caring or treating the skin, comprising 0.25 to 3% by weight of diorganopolysiloxane having formula (1) or (2).

12. A method for protecting skin and natural or sensitised hair against ultraviolet radiation, which consists in applying to the skin or hair an effective quantity of a cosmetic composition containing at least one dibenzoylemthane diorganopolysiloxane having formula (1) or (2) as defined in claim 1.

13. A method of protecting a cosmetic composition against ultraviolet radiation which consists in incorporating into said composition an effective quantity of at least one dibenzoylmethane diorganopolysiloxane having formula (1) or (2) as defined in claim 1.

* * * * *